(12) United States Patent
Zhai et al.

(10) Patent No.: US 12,272,442 B2
(45) Date of Patent: Apr. 8, 2025

(54) TRANSFER LEARNING BETWEEN DIFFERENT COMPUTER VISION TASKS

(71) Applicant: Google LLC, Mountain View, CA (US)

(72) Inventors: Xiaohua Zhai, Zurich (CH); Sylvain Gelly, Zurich (CH); Alexander Kolesnikov, Zurich (CH); Yin Ching Jessica Yung, Vienna (AT); Joan Puigcerver i Perez, Zurich (CH); Lucas Klaus Beyer, Zurich (CH); Neil Matthew Tinmouth Houlsby, Zurich (CH); Wen Yau Aaron Loh, Mountain View, CA (US); Alan Prasana Karthikesalingam, London (GB); Basil Mustafa, Zurich (CH); Jan Freyberg, London (GB); Patricia Leigh MacWilliams, London (GB); Vivek Natarajan, Sunnyvale, CA (US)

(73) Assignee: Google LLC, Mountain View, CA (US)

( * ) Notice: Subject to any disclaimer, the term of this patent is extended or adjusted under 35 U.S.C. 154(b) by 647 days.

(21) Appl. No.: 17/551,050

(22) Filed: Dec. 14, 2021

(65) Prior Publication Data
US 2022/0189612 A1 Jun. 16, 2022

Related U.S. Application Data

(60) Provisional application No. 63/125,353, filed on Dec. 14, 2020.

(51) Int. Cl.
*G16H 30/40* (2018.01)
*G06N 3/02* (2006.01)
(Continued)

(52) U.S. Cl.
CPC ............... *G16H 30/40* (2018.01); *G06N 3/02* (2013.01); *G06N 3/096* (2023.01); *G06T 3/4053* (2013.01);
(Continued)

(58) Field of Classification Search
CPC combination set(s) only.
See application file for complete search history.

(56) References Cited

U.S. PATENT DOCUMENTS

2017/0039456 A1* 2/2017 Saberian ................. G06N 3/045
2021/0287089 A1* 9/2021 Mayer ....................... G06N 3/04
(Continued)

FOREIGN PATENT DOCUMENTS

CN 109255755 A * 1/2019 ............. G06N 3/045
CN 111079843 A * 4/2020 ............... G06K 9/62
CN 111462093 A * 7/2020

OTHER PUBLICATIONS

Alsheh et al., "Association of microcalcification clusters with short-term invasive breast cancer risk and breast cancer risk factors," Scientific reports, Oct. 10, 2019, 9(1):14604.
(Continued)

*Primary Examiner* — Oneal R Mistry
*Assistant Examiner* — Justin Philip Cascais
(74) *Attorney, Agent, or Firm* — Fish & Richardson P.C.

(57) ABSTRACT

Methods, systems, and apparatus, including computer programs encoded on computer storage media, for training a neural network to perform a downstream computer vision task. One of the methods includes pre-training an initial neural network that shares layers with the neural network to perform an initial computer vision task and then training the neural network on the downstream computer vision task.

20 Claims, 3 Drawing Sheets

(51) Int. Cl.
G06N 3/096 (2023.01)
G06T 3/4053 (2024.01)
G06T 7/00 (2017.01)
G06V 10/82 (2022.01)
G16H 50/20 (2018.01)

(52) U.S. Cl.
CPC ............ *G06T 7/0012* (2013.01); *G06V 10/82* (2022.01); *G16H 50/20* (2018.01); *G06T 2207/20081* (2013.01)

(56) References Cited

U.S. PATENT DOCUMENTS

2022/0261659 A1* 8/2022 Xu ........................... G06N 3/08
2023/0114934 A1* 4/2023 Liao ......................... G06T 7/30
382/128

OTHER PUBLICATIONS

Alzubaidi et al., "Towards a better understanding of transfer learning for medical imaging: a case study," Applied Sciences, Jun. 2020, 10(13):4523.
Athiwaratkun et al., "There are many consistent explanations of unlabeled data: Why you should average," Proceedings of the 7th International Conference on Learning Representations, May 2019, 22 pages.
Barbu et al., "Objectnet: A large-scale bias-controlled dataset for pushing the limits of object recognition models," Advances in Neural Information Processing Systems, Dec. 2019, 11 pages.
Barz et al., "Do we train on test data? purging CIFAR of near-duplicates," CoRR, submitted on Feb. 1, 2019, arXiv:1902.00423v1, 5 pages.
Beery et al., "Recognition in terra incognita," CoRR, submitted on Jul. 13, 2018, arXiv:1807.04975v1,18 pages.
Berthelot et al., "ReMixMatch: Semi-supervised learning with distribution alignment and augmentation anchoring," CoRR, submitted on Feb. 13, 2020, arXiv:1911.09785v2, 13 pages.
Borji, "Objectnet dataset: Reanalysis and correction," CoRR, submitted on Apr. 4, 2020, arXiv:2004.02042v1, 31 pages.
Brown et al., "Language models are few-shot learners," Advances in Neural Information Processing Systems, Dec. 2020, 25 pages.
Chen et al., "A closer look at few-shot classification," CoRR, submitted on Apr. 8, 2019, arXiv:1904.04232v1, 17 pages.
Chen et al., "A simple framework for contrastive learning of visual representations," CoRR, submitted on Feb. 13, 2020, arXiv:2002.05709v1, 17 pages.
Chen et al., "Med3d: Transfer learning for 3d medical image analysis," CoRR, submitted on Jul. 17, 2019, arXiv:1904.00625v4, 12 pages.
Chollet, "Xception: Deep learning with depthwise separable convolutions," Proceedings of the IEEE Conference on Computer Vision and Pattern Recognition, Jul. 2017, 1251-1258.
D'Amour et al., "Underspecification presents challenges for credibility in modern machine learning," CoRR, submitted on Nov. 24, 2020, arXiv:2011.03395v1, 59 pages.
De et al., "Batch Normalization has Multiple Benefits: An Empirical Study on Residual Networks," Proceedings of the International Conference on Learning Representations, Apr. 2020, 11 pages.
Deng et al., "Imagenet: A large-scale hierarchical image database," Proceedings of the IEEE Conference on Computer Vision and Pattern Recognition, Jun. 2009, 248-255.
Djolonga et al., "On robustness and transferability of convolutional neural networks," CoRR, submitted on Jul. 16, 2020, arXiv:2007.08558v1, 24 pages.
Dosovitskiy et al., "An image is worth 16x16 words: Transformers for image recognition at scale," CoRR, submitted on Oct. 22, 2020, arXiv:2010.11929v1, 21 pages.
Esteva et al., "Dermatologist-level classification of skin cancer with deep neural networks," Nature, Jan. 25, 2017, 542(7639):115-118.
Geyer et al., "Transfer learning by adaptive merging of multiple models," Proceedings of Machine Learning Research, May 2019, 102:185-196.
Girshick et al., "Rich feature hierarchies for accurate object detection and semantic segmentation," Proceedings of the IEEE Conference on Computer Vision and Pattern Recognition, Jun. 2014, 580-587.
github.com [online], "TensorFlow-Slim image classification model library," Jan. 2016, retrieved on Dec. 6, 2023, retrieved from URL: <https://github.com/tensorflow/models/tree/master/research/slim>, 11 pages.
Goyal et al., "Accurate, Large Minibatch SGD: Training ImageNet in 1 Hour," CoRR, submitted on Apr. 30, 2018, arXiv:1706.02677v2, 12 pages.
Graziani et al., "Visualizing and interpreting feature reuse of pretrained CNNs for histopathology," MVIP 2019: Irish Machine Vision and Image Processing Conference Proceedings, Aug. 2019, 4 pages.
Gulshan et al., "Development and validation of a deep learning algorithm for detection of diabetic retinopathy in retinal fundus photographs," JAMA, Dec. 13, 2016, 316(22):2402-2410.
Guo et al., "On calibration of modern neural networks," Proceedings of the 34th International Conference on Machine Learning (PMLR), Aug. 2017, 70:1321-1330.
He et al., "Deep residual learning for image recognition," Proceedings of the IEEE Conference on Computer Vision and Pattern Recognition, Jun. 2016, 770-778.
He et al., "Identity mappings in deep residual networks," Proceedings of Computer Vision—ECCV 2016, Oct. 2016, 630-645.
He et al., "Momentum contrast for unsupervised visual representation learning," CoRR, submitted on Nov. 14, 2019, arXiv:1911.05722v2, 11 pages.
He et al., "Rethinking imagenet pre-training," Proceedings of the IEEE/CVF International Conference on Computer Vision, Oct. 27-Nov. 2, 2019, 4918-4927.
He et al., "Sample-efficient deep learning for COVID-19 diagnosis based on CT scans," MedRxiv, Apr. 17, 2020, 10 pages.
Heker et al., "Joint liver lesion segmentation and classification via transfer learning," CoRR, submitted on Apr. 26, 2020, arXiv:2004.12352v1, 5 pages.
Henaff et al., "Data-Efficient Image Recognition with Contrastive Predictive Coding," CoRR, submitted on May 22, 2019, arXiv:1905.09272v1, 11 pages.
Hermans et al., "In defense of the triplet loss for person re-identification," CoRR, submitted on Nov. 21, 2017, arXiv:1703.07737v4, 17 pages.
Hinton et al., "Distilling the knowledge in a neural network," CoRR, submitted on Mar. 9, 2015, arXiv:1503.02531v1, 9 pages.
Huang et al., "GPipe: Efficient training of giant neural networks using pipeline parallelism," CoRR, submitted on Nov. 16, 2018, arXiv:1811.06965v1, 11 pages.
Huh et al., "What makes imagenet good for transfer learning?" CoRR, submitted on Aug. 30, 2016, arXiv:1608.08614v1, 15 pages.
Ioffe et al., "Batch normalization: Accelerating deep network training by reducing internal covariate shift," Proceedings of the 32nd International Conference on International Conference on Machine Learning (JMLR), Jul. 2015, 37:448-456.
Ioffe, "Batch Renormalization: Towards reducing minibatch dependence in batch-normalized models," Proceedings of the 31st International Conference on Neural Information Processing Systems, Dec. 2017, 1942-1950.
Irvin et al., "CheXpert: A large chest radiograph dataset with uncertainty labels and expert comparison," Proceedings of the AAAI Conference on Artificial Intelligence, Jul. 17, 2019, 33(1):590-597.
Izmailov et al., "Averaging weights leads to wider optima and better generalization," CoRR, submitted on Feb. 25, 2019, arXiv:1803.05407v3, 12 pages.
Joulin et al., "Learning visual features from large weakly supervised data," Proceedings of Computer Vision—ECCV 2016, Oct. 2016, pp. 67-84.
Jouppi et al., "In-Datacenter performance analysis of a tensor processing unit," Proceedings of the 44th Annual International Symposium on Computer Rrchitecture, Jun. 24, 2017, 12 pages.

(56) References Cited

OTHER PUBLICATIONS

Kaplan et al., "Scaling laws for neural language models," CoRR, submitted on Jan. 23, 2020, arXiv:2001.08361v1, 30 pages.
Kingma et al., "Adam: A method for stochastic optimization," CoRR, submitted on Dec. 22, 2014, arXiv:1412.6980v1, 9 pages.
Kolesnikov et al., "Big transfer (bit): General visual representation learning," CoRR, submitted on Mar. 30, 2020, arXiv:1912.11370v2, 25 pages.
Kornblith et al., "Do better imagenet models transfer better?" Proceedings of the IEEE/CVF Conference on Computer Vision and Pattern Recognition, Jun. 2019, 2661-2671.
Kornblith et al., "Similarity of neural network representations revisited," Proceedings of the International Conference on Machine Learning (PMLR), May 24, 2019, 97:3519-3529.
Krizhevsky, "Learning multiple layers of features from tiny images," Technical Report, University of Toronto, Apr. 8, 2009, 60 pages.
Kuznetsova et al., "The Open Images Dataset V4: Unified image classification, object detection, and visual relationship detection at scale," CoRR, submitted on Nov. 2, 2018, arXiv:1811.00982v1, 20 pages.
Li et al., "An exponential learning rate schedule for deep learning," CoRR, submitted on Oct. 16, 2019, arXiv:1910.07454v1, 27 pages.
Li et al., "Explicit inductive bias for transfer learning with convolutional networks," Proceedings of the International Conference on Machine Learning (PMLR), Jul. 3, 2018, 80:2825-2834.
Li et al., "Learning visual n-grams from web data," Proceedings of the IEEE International Conference on Computer Vision, Oct. 2017, 4183-4192.
Liang et al., "A transfer learning method with deep residual network for pediatric pneumonia diagnosis," Computer Methods and Programs in Biomedicine, Apr. 2020, 187:104964.
Lin et al., "Focal loss for dense object detection," Proceedings of the IEEE International Conference on Computer Vision, Oct. 2017, 2980-2988.
Lin et al., "Microsoft COCO: Common objects in context," Proceedings of Computer Vision—ECCV 2014, Sep. 2014, 740-755.
Liu et al., "A deep learning system for differential diagnosis of skin diseases," Nature Medicine, Jun. 2020, 26(6):900-908.
Liu et al., "Detecting cancer metastases on gigapixel pathology images," CoRR, submitted on Mar. 3, 2017, arXiv:1703.02442v1, 13 pages.
Long et al., "Fully convolutional networks for semantic segmentation," Proceedings of the IEEE Conference on Computer Vision and Pattern Recognition, Jun. 2015, 3431-3440.
Loshchilov et al., "SGDR: Stochastic gradient descent with warm restarts," CoRR, submitted on Aug. 13, 2016, arXiv:1608.03983v1, 9 pages.
Mahajan et al., "Exploring the limits of weakly supervised pretraining," Proceedings of the European Conference on Computer Vision, Sep. 2018, 181-196.
McKinney et al., "International evaluation of an AI system for breast cancer screening," Nature, Jan. 2, 2020, 577(7788):89-94.
Menegola et al., "Knowledge transfer for melanoma screening with deep learning," Proceedings of the IEEE 14th International Symposium on Biomedical Imaging, Apr. 2017, 297-300.
Nakamura et al., "Revisiting Fine-tuning for few-shot learning," CoRR, submitted on Oct. 1, 2019, arXiv:1910.00216v1, 10 pages.
Neyshabur et al., "What is being transferred in transfer learning?" CoRR, submitted on Aug. 26, 2020, arXiv:2008.11687v1, 34 pages.
Ngiam et al., "Domain adaptive transfer learning with specialist models," CoRR, submitted on Nov. 16, 2018, arXiv:1811.07056v1, 10 pages.
Nilsback et al., "Automated flower classification over a large number of classes," Sixth Indian Conference on Computer Vision, Graphics & Image Processing, Dec. 16, 2008, 722-729.
Pan et al., "A survey on transfer learning," IEEE Transactions on Knowledge and Data Engineering, Oct. 16, 2009, 22(10):1345-1359.
Parkhi et al., "Cats and dogs," IEEE Conference on Computer Vision and Pattern Recognition, Jun. 2012, 3498-3505.
Peyre et al., "Weakly-supervised learning of visual relations," CoRR, submitted on Jul. 29, 2017, arXiv:1707.09472v1, 16 pages.
Qiao et al., "Micro-batch training with batch-channel normalization and weight standardization," CoRR, submitted on Aug. 9, 2020, arXiv:1903.10520v2, 15 pages.
Qiao et al., "Weight standardization," CoRR, submitted on Mar. 25, 2019, arXiv:1903.10520v1, 10 pages.
Raghu et al., "Transfusion: Understanding transfer learning for medical imaging," Proceedings of the 33rd International Conference on Neural Information Processing Systems, Dec. 2019, 3347-3357.
Raghu et al., "Transfusion: Understanding transfer learning with applications to medical imaging," CoRR, submitted on Feb. 14, 2019, arXiv:1902.07208v1, 22 pages.
Rajpurkar et al., "CheXNet: Radiologist-level pneumonia detection on chest x-rays with deep learning," CoRR, submitted on Nov. 14, 2017, arXiv:1711.05225v1, 7 pages.
Rajpurkar et al., "CheXpedition: Investigating generalization challenges for translation of chest x-ray algorithms to the clinical setting," CoRR, submitted on Mar. 11, 2020, arXiv:2002.11379v2, 8 pages.
Rebuffi et al., "Learning multiple visual domains with residual adapters," Proceedings of the 31st International Conference on Neural Information Processing Systems, Dec. 2017, 506-516.
Rosenfeld et al., "A constructive prediction of the generalization error across scales," Proceedings of the 8th International Conference on Learning Representations, Apr. 2020, 30 pages.
Russakovsky et al., "Imagenet large scale visual recognition challenge," International Journal of Computer Vision, Dec. 2015, 115:211-252.
Shetty et al., "Not using the car to see the sidewalk—Quantifying and controlling the effects of context in classifcation and segmentation," CoRR, submitted on Dec. 17, 2018, arXiv:1812.06707v1, 14 pages.
Simonyan et al., "Very deep convolutional networks for large-scale image recognition," CoRR, submitted on Sep. 4, 2014, arXiv:1409.1556v1, 10 pages.
Snell et al., "Prototypical networks for few-shot learning," Proceedings of the 31st International Conference on Neural Information Processing Systems, Dec. 2017, 4080-4090.
Sohn et al., "Fixmatch: Simplifying semi-supervised learning with consistency and confidence," CoRR, submitted on Jan. 21, 2020, arXiv:2001.07685v1, 14 pages.
Steed et al., "Image representations learned with unsupervised pre-training contain human-like biases," CoRR, submitted on Oct. 28, 2020, arXiv:2010.15052v1, 20 pages.
Sun et al., "Revisiting Unreasonable Effectiveness of Data in Deep Learning Era," Proceedings of the IEEE International Conference on Computer Vision (ICCV), Oct. 2017, 843-852.
Sung et al., "Learning to compare: Relation network for few-shot learning," Proceedings of the IEEE Conference on Computer Vision and Pattern Recognition, Jun. 2018, 1199-1208.
Szegedy et al., "Going deeper with convolutions," Proceedings of the IEEE Conference on Computer Vision and Pattern Recognition, Jun. 2015, 9 pages.
Szegedy et al., "Rethinking the inception architecture for computer vision," Proceedings of the IEEE Conference on Computer Vision and Pattern Recognition, Jun. 2016, 2818-2826.
Tan et al., "EfficientNet: Rethinking model scaling for convolutional neural networks," Proceedings of the International conference on machine learning (PMLR), May 24, 2019, 97:6105-6114.
Thomee et al., "The New Data and New Challenges in Multimedia Research," CoRR, submitted on Mar. 5, 2015, arXiv:1503.01817v1, 7 pages.
Touvron et al., "Fixing the train-test resolution discrepancy," Proceedings of the 33rd International Conference on Neural Information Processing Systems, Dec. 2019, 8252-8262.
Tschannen et al. "Self-supervised learning of video-induced visual invariances," CoRR, submitted on Dec. 5, 2019, arXiv:1912.02783v1, 16 pages.
Van Laarhoven, "L2 regularization versus batch and weight normalization," CoRR, submitted on Jun. 16, 2017, arXiv:1706.05350v1, 9 pages.

(56) References Cited

OTHER PUBLICATIONS

Vinyals et al., "Matching networks for one shot learning," Proceedings of the 30th International Conference on Neural Information Processing Systems, Dec. 2016, 3637-3645.
Wang et al., "ChestX-ray8: Hospital-scale chest x-ray database and benchmarks on weakly-supervised classification and localization of common thorax diseases," Proceedings of the IEEE Conference on Computer Vision and Pattern Recognition, Jul. 2017, 2097-2106.
Willemink et al., "Preparing medical imaging data for machine learning," Radiology, Apr. 2020, 295(1):4-15.
Wu et al., "Group normalization," Proceedings of Computer Vision—ECCV 2018, Sep. 2018, 3-19.
Xie et al., "Aggregated residual transformations for deep neural networks," Proceedings of the IEEE Conference on Computer Vision and Pattern Recognition, Jul. 2017, 1492-1500.
Xie et al., "Dual network architecture for few-view CT-trained on ImageNet data and transferred for medical imaging," Developments in X-ray Tomography XII, Sep. 10, 2019, 11113:184-194.
Xie et al., "Self-training with noisy student improves imagenet classification," Proceedings of the IEEE/CVF conference on computer vision and pattern recognition, Jun. 2020, pp. 10687-10698.
Yalniz et al., "Billion-scale semi-supervised learning for image classification," CoRR, submitted on May 2, 2019, arXiv:1905.00546v1, 12 pages.
Yosinski et al., "How transferable are features in deep neural networks?" Proceedings of the 27th International Conference on Neural Information Processing Systems, Dec. 2014, 3320-3328.
Yun et al., "CutMix: Regularization Strategy to Train Strong Classifiers with Localizable Features," CoRR, submitted on May 13, 2019, arXiv:1905.04899v1, 14 pages.
Zhai et al., "A large-scale study of representation learning with the visual task adaptation benchmark," CoRR, submitted on Feb. 21, 2020, arXiv:1910.04867v2, 33 pages.
Zhai et al., "S4L: Self-supervised semi-supervised learning," Proceedings of the IEEE/CVF International Conference on Computer Vision, Oct. 27-Nov. 2, 2019, 1476-1485.
Zhang et al., "mixup: Beyond empirical risk minimization," CoRR, submitted on Oct. 25, 2017, arXiv:1710.09412v1, 11 pages.

* cited by examiner

TRANSFER LEARNING BETWEEN DIFFERENT COMPUTER VISION TASKS

CROSS-REFERENCE TO RELATED APPLICATION

This application claims priority to U.S. Provisional Application No. 63/125,353, filed on Dec. 14, 2020. The disclosure of the prior application is considered part of and is incorporated by reference in the disclosure of this application.

BACKGROUND

This specification relates to training neural networks.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system implemented as computer programs on one or more computers in one or more locations that trains, using transfer learning, a neural network that is configured to perform a particular computer vision task. The particular computer vision task will be referred to as a "downstream computer vision task."

Particular embodiments of the subject matter described in this specification can be implemented so as to realize one or more of the following advantages.

The transfer learning techniques described in this specification improve sample efficiency and simplify hyperparameter tuning when training deep neural networks for vision, resulting in improved performance on the downstream task. This improved performance can be achieved even when the initial task and the downstream task operate on images from completely different domains, e.g., when the initial task operates on natural images while the downstream task requires processing medical images, when the amount of training data for the downstream task is very limited, or both.

In other words, this specification describes techniques for modifying the transfer learning paradigm to achieve effective transfer even when significant differences between the training data for the initial task and the downstream task exist.

For example, by using group normalization and weight standardization within the backbone layers that are shared between the initial and downstream neural networks, the system can significantly increase the usefulness of the representations learned during pre-training to the downstream task.

As another example, by adjusting the hyperparameters of the supervised learning technique after pre-training and before starting the fine-tuning on the downstream task based on various factors, the system can customize the fine-tuning to the size and characteristics of the downstream training data set to maximize the performance of the downstream neural network.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
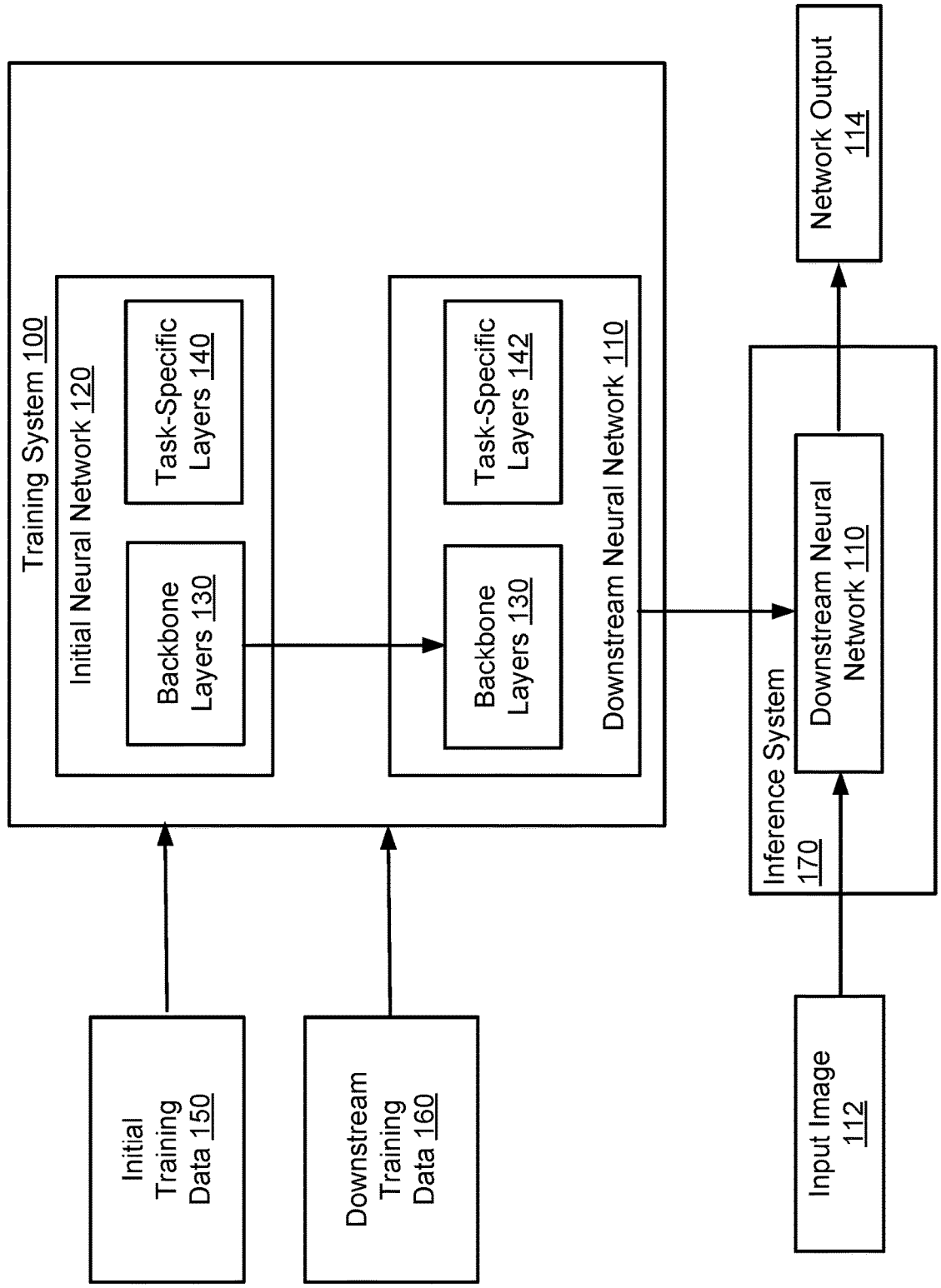
FIG. 1 shows an example training system.

FIG. 1 shows an example training system 100. The training system 100 is an example of a system implemented as computer programs on one or more computers in one or more locations, in which the systems, components, and techniques described below can be implemented.

The system 100 trains, using an initial neural network 120, a downstream neural network 110 that is configured to perform a particular computer vision task. The particular computer vision task will be referred to as a "downstream computer vision task" and the neural network 120 will be referred to as a "downstream" neural network because it is configured to perform the downstream computer vision task.

After training, an inference system 170 deploys the trained downstream neural network 110 on one or more computing devices to perform inference, i.e., to generate new network outputs 114 for the downstream computer vision task for new input images 112.

The downstream computer vision task can generally be any computer vision task that requires receiving an input that includes one or more images 112 and processing the input using a neural network to generate an output 114.

For example, the task may be image classification and the output generated by the downstream computer vision task for a given image may be scores for each of a set of object categories, with each score representing an estimated likelihood that the image contains an image of an object belonging to the category.

As another example, the task can be image embedding generation and the output generated by the downstream computer vision task can be a numeric embedding of the input image.

As yet another example, the task can be object detection and the output generated by the downstream computer vision task can identify locations in the input image at which particular types of objects are depicted.

As yet another example, the task can be image segmentation and the output generated by the downstream computer vision task can assign each pixel of the input image to a category from a set of categories.

The system 100 trains the downstream neural network 110 through transfer learning.

In particular, the system 100 first pre-trains the initial neural network 120 to perform on an initial computer vision task.

That is, the system obtains training data 150 for the initial computer vision task and trains the initial neural network 120 on the training data 150 to perform the initial computer vision task to determine pre-trained values of the parameters of the initial neural network 120.

The initial task and the downstream tasks are generally different tasks. For example, the initial task and the downstream task can both be image classification, but can require classifying different types of images into different sets of classes. Such examples are described in more detail below with reference to FIG. 2.

As another example, the initial task may be a classification task while the downstream task may be object detection or another regression task.

Even though the two neural networks are configured to perform different tasks, the initial neural network 120 and the downstream neural network 110 share some neural network layers, i.e., the initial neural network 120 includes some of the same neural network layers as the downstream neural network that will be trained on the downstream task.

In particular, the initial neural network 120 includes a set of backbone neural network layers 120 that are shared with the downstream neural network 110 and a set of task-specific neural network layers 140 that are not shared with the downstream neural network 110.

Similarly, the downstream neural network 110 includes the same set of backbone neural network layers 120 and a set of task-specific neural network layers 142 that are not shared with the initial neural network 120.

For example, the initial neural network 120 and the downstream neural network 110 can share a set of initial layers, i.e., the backbone layers, 120, that receive an input that includes one or more images and process the input to generate a representation (a "visual representation") of the input.

The initial neural network 120 can then include one more additional layers, i.e., the task-specific layers 140, that process the visual representation to generate an output for the initial computer vision task while the downstream neural network 110 can include different additional layers, i.e., task-specific layers 142, that process the visual representation to generate an output for the downstream task.

Thus, by pre-training the initial neural network 120, the system 100 determines pre-trained values for the backbone layers 130 and the task-specific layers 140.

The system 100 then trains the trains the downstream neural network 110 on training data 160 for the downstream computer vision task starting from the pre-trained values of the parameters of backbone layers 130 that are shared with the initial neural network and newly initialized values for the task-specific layers 142 that are not shared. For example, prior to training the downstream neural network 110, the system can initialize the values of the task-specific layers 142 by randomly sampling weight values from a pre-determined distribution or using a different conventional parameter initialization technique.

In more detail, both the downstream neural network 110 and the initial neural network 120 are generally convolutional neural networks that include a set of convolutional layers that receive an input image and process the input image to generate the visual representation of the image. This set of convolutional layers are the backbone layers 130 that are shared between the two neural networks.

Each of the convolutional layers in this set of convolutional layers is configured to receive, as input, an input feature map having dimension $H1 \times W1 \times C1$, where H1 and W1 are the spatial dimensions of the input feature map and C1 is the number of channels in the input feature map. Each layer then generates, as output, an output feature map having dimensions $H2 \times W2 \times C2$, where H2 and W2 are the spatial dimensions of the output feature map and C2 is the number of channels, at least in part by performing a convolutional between the input feature map and a kernel of the layer. The values of H1, H2, W1, W2, C1, and C2 can differ for different layers depending on the configuration of the neural network. For example, when the inputs are RGB images, the input to the first convolutional layer in the network will be an $H \times W \times 3$ image, where $H \times W$ are the dimensions of the input image.

The task-specific layers 140 in the initial neural network then receive this visual representation and process the visual representation to generate the output for the initial task. For example, when the initial task is image classification of a single image the task-specific layers 140 can include one or more fully-connected layers followed by a softmax layer that generates the probability distribution over the object categories.

The task-specific layers 142 in the downstream neural network 110 then receive this visual representation and process the visual representation to generate the output for the downstream task.

For example, when the downstream task is image classification of a single image, the task-specific layers 142 can include one or more fully-connected layers followed by a softmax layer that generates the probability distribution over the object categories.

In some cases, the initial task can require processing one image while the downstream task can require processing multiple images. In these cases, for the downstream task, the task-specific layers 142 can include a combining layer that receives the respective visual representations generated by the backbone layers 130 for each of the multiple images and combines them, e.g., averages or concatenates, to generate a combined representation, one or more fully-connected layers that process the combined representation and that are followed by a softmax layer that generates the probability distribution over the object categories or by one or more logistic regression nodes when the downstream task is composed of one or more binary classifications.

The system 100 can use any of a variety of convolutional backbones as the backbone layers 130. For example, the system can use a ResNet backbone that is made up of residual convolutional blocks or another backbone architecture that maps input images to a feature map of specified dimensionality that can serve as the visual representation.

However, many of these backbones are ill-suited for the types of transfer learning that the system 100 performs, e.g., due to the difficulties caused by mismatches between initial and downstream tasks that are discussed below with reference to FIG. 2 and due to mismatches in batch size and training data set between the initial training data and the downstream training data.

Thus, to account for this and to improve how well the representations transfer between initial and downstream tasks, the system 100 modifies the backbone layers 140 so that some or all of the convolutional layers in the backbone layers 140 have weight standardization (WS) and are each followed by a respective group normalization (GN) layer.

GN layers receive as input a feature map, e.g., having dimensions $H3 \times W3 \times C3$, and divide the channels of the feature map into multiple groups. For each group, the GN layer then computes the mean and standard deviations of the values in the feature map that have a channel index that is within the group and normalizes each value that has a channel index that within the group using the computed mean and standard deviation for the group. The GN layer then applies a learned per-channel linear transformation to the normalized values to generate the output feature map for the GN layer.

Convolutional layers with WS re-parameterize the weights of the layer, i.e., the weights in the kernel of the layer, as the output of a standardization function that is applied to a set of unstandardized weights of the layer, i.e., so that each weight is generated from a corresponding unstandardized weight by applying the standardization function. During training, the unstandardized weights of the layer are updated through gradient descent while the "standardized weights" that are output by the standardization function are used to compute the output feature maps for the layer for the forward pass of the neural network. In particular, the standardization function computes, for each output channel, the mean and standard deviations of the unstandardized weights corresponding to the output channel and then normalizes each unstandardized weight corresponding to that output channel to generate the standardized weights corresponding to that output channel.

Many state-of-the-art vision models use Batch Normalization (BN) to stabilize training. However, using BN in the backbone layers 130 is detrimental to the described transfer learning approach for several reasons. For example, when training large models with small per-device batches, BN performs poorly or incurs inter-device synchronization cost. As will be described in more detail below, the downstream tasks can have less training data than the initial task, requiring these smaller batch sizes that can be problematic for BN. Second, due to the requirement imposed by BN to update running statistics so that the updated statistics can be used after training, BN is detrimental for transfer, i.e., because the running statistics may not accurately reflect the properties of both the downstream and initial tasks. By combining GN and WS, i.e., instead of using BN, these difficulties are mitigated. Moreover, using the combination of GN and WS in the backbone layers 130 has a significant positive impact on transfer learning and works well even when larger batch sizes are used for the initial task training while smaller batch sizes are used for the downstream task training.

Figure 2:
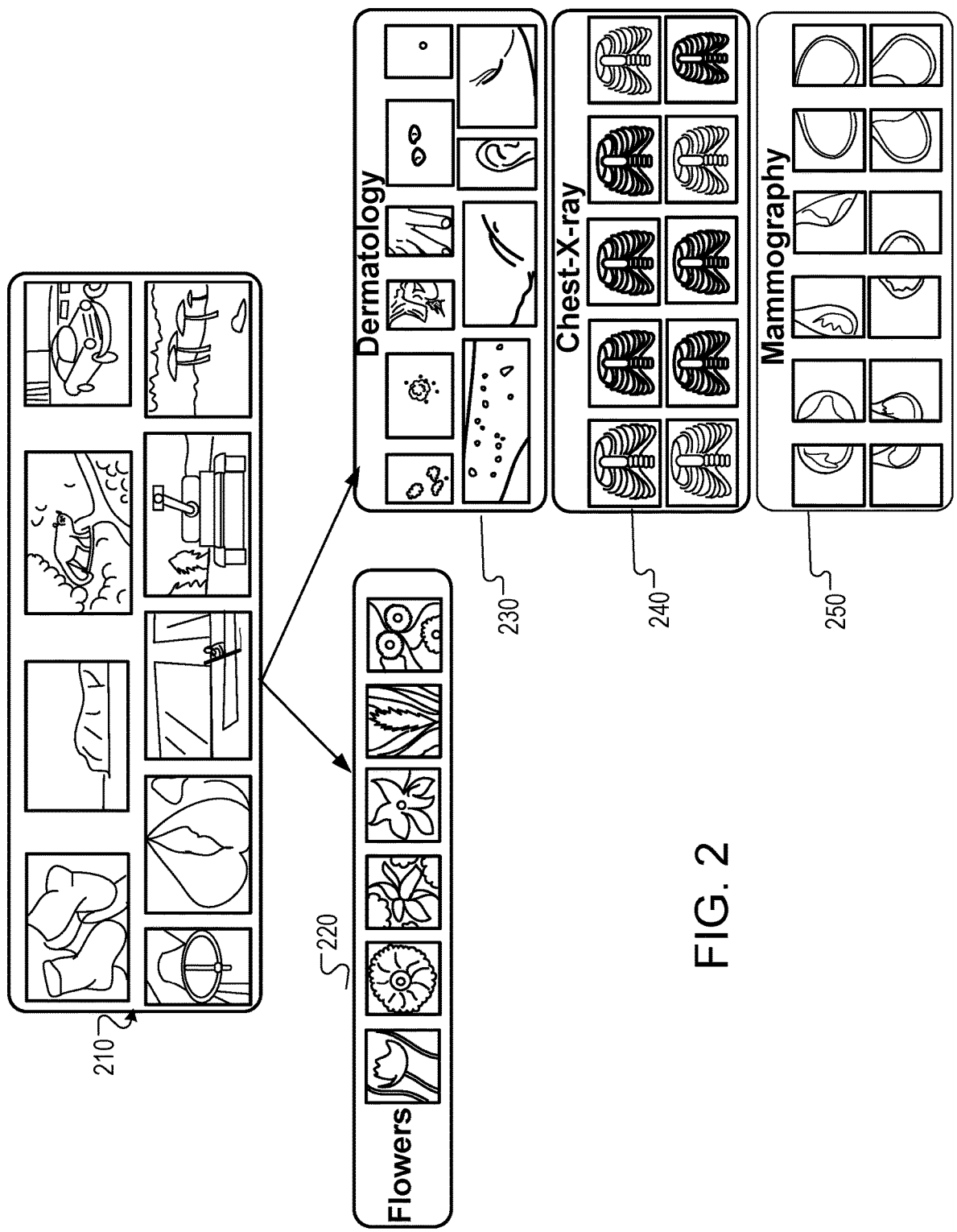
FIG. 2 shows examples of training images for initial and downstream computer vision tasks.

FIG. 2 shows an example of training images for initial and downstream computer vision tasks.

In particular, the example of FIG. 2 shows an example set of training images 210 from an example initial downstream computer vision task. The example initial downstream computer task is a natural object image classification task, i.e., requires the neural network to classify each image into one of multiple object categories that each correspond to a different category of natural object. A "natural object" is one that can be seen by a human in the real-world. As can be seen from the example of FIG. 2, the set of training images 210 include images of a variety of different natural objects, e.g., animals, plants, automobiles, items of clothing, boats, manmade objects like bells, and so on.

Natural object image classification tasks can make good candidates for the pre-training, i.e., for serving as the initial task, because a large amount of labeled data for these tasks is widely available. As one example, the ImageNet database includes millions of images of natural objects, each with a corresponding label identifying which object(s) are depicted in the image.

However, the downstream tasks can be quite different from the initial natural object classification ask.

FIG. 2 shows four example sets of images 220, 230, 240, and 250 from four different potential downstream tasks.

The set of images 220 is an example set of images for a possible downstream task that requires classifying different types of flowers. Thus, while this task also requires processing images that depict natural objects, i.e., flowers, the task requires a much more fine-grained classification that the initial natural object classification task. Moreover, while a large amount of labeled examples are available for the initial task, only a much smaller amount of images are likely to be available for this downstream task. For example, because distinguishing between types of flowers requires specialized knowledge, it may be difficult to obtain accurate labels for this task.

The described transfer learning techniques allow the images for the initial task to be used to improve performance on the downstream task, even when the downstream task requires fine-gained classification and has a relatively small set of training data.

The sets of images 230, 240, and 250 are images for medical imaging tasks. That is, each set of images 230, 240, and 250 are from a medical domain, i.e., are captured for use in medical diagnosis using a respective medical imaging device. In other words, for these tasks, the downstream task is from the medical domain but the initial task is from a different domain, i.e., the natural image domain.

In particular, the set of images 230 are camera images of a portion of a human body, i.e., dermatology images of different regions of skin on a human body. As a particular example, these images can be used for a skin condition diagnosis task, i.e., a task where the object categories are areas of skin indicative of a person having one or more medical conditions. In some cases, the task may require processing multiple images of the same person's skin in order to generate the output for the task.

The set of images 240 and the set of images 250 are X-ray images taken with an X-ray imaging device.

In particular, the set of images 240 are chest X-rays that can be used for a chest X-ray interpretation task, i.e., a task that requires respective binary classifications for each of one or more pathologies that might be detected from a chest X-ray, and the set of images 240 are mammography images that can be used for a mammography task, i.e., a task where the object categories are various categories related to the presence or absence of breast cancer. In some cases, the mammography task may require processing multiple mammography images to generate the output for the task.

As can be seen from the example of FIG. 2, downstream tasks that require classifying medical images present a large domain shift when transferring from natural images. For example, medical images are typically much higher resolution, some types of medical images have non-RGB channels, and models often rely on small, local variations in texture to interpret the images and detect pathologies of interest.

Other factors that distinguish medical images from natural images include the fact that medical images for a given domain have standardized views; images are frequently gray-scale; resolution is usually significantly higher; and the task relevant features tend to be small patches or local texture variations instead of semantic higher level features as compared to natural images.

Moreover, labeled medical images can be difficult to obtain, limiting the size of the training data for these downstream medical imaging tasks.

These differences, i.e., the domain gap between medical and natural images and the fine-grained classification required for some natural object classification tasks, make conventional transfer learning techniques ill-suited for being applied to improve the performance of the downstream neural network on many tasks like the ones described above.

The described techniques, however, modify the transfer learning paradigm to improve the performance of the transfer learning, i.e., to improve the quality of the trained downstream neural network. In addition to modifying the architecture of the backbone layers using GN and WS as described above, the system can also modify and adapt the supervised learning techniques used to train the neural networks to improve the learning transfer. This will be described in more detail below with reference to FIG. 3.

Figure 3:
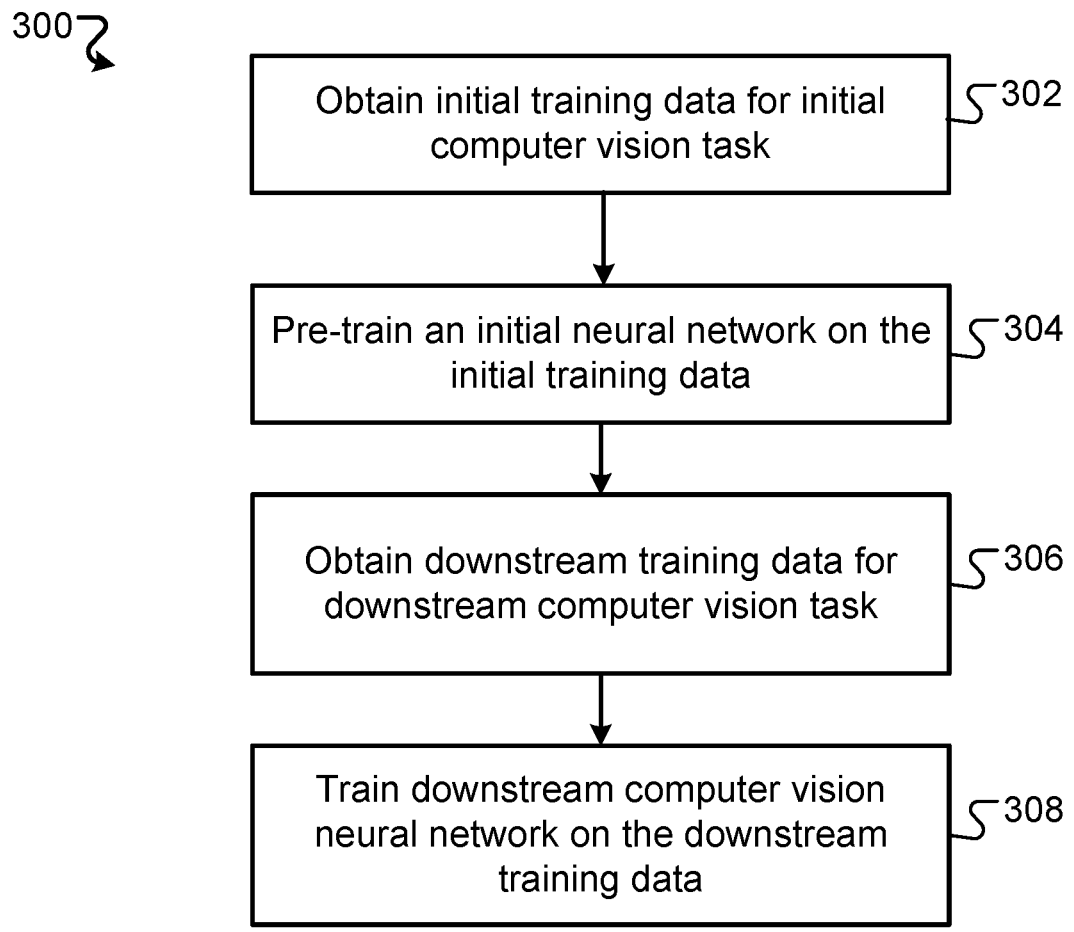
FIG. 3 is a flow diagram of an example process for training a downstream neural network.

FIG. 3 is a flow diagram of an example process 300 for training the downstream neural network. For convenience, the process 300 will be described as being performed by a system of one or more computers located in one or more locations. For example, a training system, e.g., the training system 100 of FIG. 1, appropriately programmed, can perform the process 300.

The system obtains training data for the initial computer vision task (step 302).

For example, when the initial task is a classification task, the training data includes a plurality of training examples, with each training example including (i) one or more images and (ii) a label that identifies one or more ground truth object categories for the one or more images from a set of object categories for the initial task.

A "ground truth" object category is a category to which the corresponding image(s) should be assigned by performing the corresponding task and can be determined based on, e.g., inputs from a user or using auto-labeling techniques.

The system pre-trains the initial neural network on the training data for the initial computer vision task to determine pre-trained values of the respective layer parameters of each of the layers of the initial neural network, including the backbone layers that are shared with the downstream neural network (step 304).

As described above, the backbone layers include a set of convolutional layers, some or all of which have weight standardization (WS) and are followed by a corresponding group normalization (GN) layer. Arranging the backbone layers in this configuration can assist in ensuring that the representations learned by the backbone layers during the pre-training generalize to the downstream task, thereby resulting in improved performance of the downstream neural network after the downstream neural network is trained.

The system can generally use any appropriate supervised learning technique to train the initial neural network. Specific techniques for training the initial neural network that can improve the quality of the trained downstream neural network are described in more detail below.

The system obtains training data for the downstream computer vision task (step 306). For example, when the downstream task is a classification task, the training data includes a plurality of training examples, with each training example including (i) one or more images and (ii) a label that identifies one or more ground truth object categories from a set of object categories for the downstream task.

The system trains the downstream neural network on the training data for the downstream computer vision task to determine trained values of the respective layer parameters of the layers of the downstream neural network (step 308).

In particular, the system trains the downstream neural network starting from the pre-trained values of the parameters of the backbone layers, such that, as a result of the training, the system determines trained values of the parameters of the backbone layers, including the convolutional layers with WS that are followed by GN layers, starting from the pre-trained values while determining trained values of the other layers of the downstream neural network starting from newly initial parameter values.

Generally, the system can train the downstream neural network and the initial neural network using any appropriate supervised learning technique, e.g., any gradient-descent based technique that optimize an appropriate objective function for the respective task.

However, in some cases, the system modifies the training of the downstream neural network, the initial neural network, or both, to improve the performance of the downstream neural network on the downstream task after training.

As a particular example, the system can apply a heuristic that is based on the size of the training data, i.e., how many training examples are in the training data, for the downstream computer vision task to determine whether and, if so, how to modify the hyperparameters of the supervised learning technique used for the pre-training when training on the downstream task.

For example, the system can define a set of scale regimes, each scale regime corresponding to a different range of numbers of training examples. As one example, a small task can be one with fewer than 20,000 training examples, a medium task can be one with at least 20,000 but fewer than 500,000 training examples, and a large task can be one with more than 500,000 training examples. The system can then determine how to modify the hyperparameters based on which scale regime the downstream tasks fall into.

As one example of a hyperparameter modification, the system can determine how many training steps to perform during the training of the neural network on the training data for the downstream computer vision task based on the size of the training data for the downstream computer vision task, i.e., based on how many images are in the training data. A "training step" refers to the training of a neural network on one batch of training data to update the parameters of the neural network. Generally, the system can set the number of training steps so that the system trains for a larger number of training steps when the training data is larger. As a particular example, the system can determine a respective number of training steps for each scale regime, with larger scale regimes having larger numbers of training steps. In the small medium large example given above, the system can train for 500 steps on small tasks, for 10000 steps on medium tasks, and for 20000 steps on large tasks.

As another example of a hyperparameter modification, the system can determine whether to perform a particular data augmentation technique during the training of the neural network on the training data for the downstream computer vision task based on the size of the training data for the downstream computer vision task, i.e., based on how many images are in the training data. As a particular example, the system can determine that, for one or more regimes corresponding to the smallest training data sizes, the system should not perform the data augmentation technique, but that the system should perform the technique for the remaining regimes. In the small medium large example given above, the system can determine not to perform the technique on small tasks, but determine to perform the technique on medium tasks and on large tasks. Any of a variety of augmentation techniques that can serve to regularize the training to, in some cases, assist the downstream neural network in generalizing better to examples outsides of the training data after training can be used. One example of such a technique is MixUp, which is described in more detail in Zhang, H., Cisse, M., Dauphin, Y. N., Lopez-Paz, D.: mixup: Beyond empirical risk minimization, ICLR 2017. In some implementations, the system does not train with the data augmentation technique during the training on the initial task.

As another particular example, the system can determine how to resize input images to a fixed resolution during the training of the neural network on the training data for the downstream computer vision task based on an original size of the images in the training data for the downstream computer vision task. In particular, in order to process an image using the downstream neural network during training, the system generally resizes the input image to a first fixed resolution. Optionally, the system can then take a random crop that has a second fixed resolution that is provided as input to the network. Further optionally, the system can flip the cropped image along some axis, e.g., perform a horizontal flip, before providing the image as input to the network. The system can determine the first fixed resolution and, when used, the second fixed resolution based on the initial resolution of the images in the training set. As one example, the system can resize input images with area smaller than 96×96 pixels to 160×160 pixels, and then take a random crop of 128×128 pixels. As another example, the system can resize larger images than 96×96 to 448×448 and take a 384×384-sized crop. As yet another example, the system can resize larger images than 96×96 to 512×512 and then crop to 480×480.

In some of these examples, the system can, after the training of the neural network on the training data for the downstream computer vision task, fine-tune the neural network to operate on images that have a scaled up resolution relative to the fixed resolution. That is, after the training, the system can fine-tune, i.e., train for one or more additional training steps on the downstream task on the downstream training data, with images that have a different, scaled up resolution, i.e., the original resolution of the images in the downstream training data or a different resolution that will be used at inference time.

As another particular example, the system can pre-train the initial neural network on training data for the initial computer vision task by training the initial neural network with weight decay, but then train the neural network on training data for the downstream computer vision task without weight decay. That is, the system can modify the supervised learning technique after the pre-training to no longer use weight decay. Some supervised learning techniques, after each training step in which a gradient is computed, subtract, from the current values of the network parameters, an update that is determined by applying an optimizer, e.g., the SGD learning rate, adafactor, Adamn, or rmsprop, to the gradient computed at the training step to determine updated values of the parameters. Weight decay refers to, after each gradient step, subtracting not only the update to the current values of the network parameters but also a weight decay constant multiplied by the sum of the squares of the current values. When weight decay is used, this constant is set to a non-zero value, e.g., a number in the range of 0.0001 to 0.000001. When weight decay is not used, this constant is set to zero and the additional subtraction is not performed.

As another particular example, the system can pre-train the initial neural network on training data for the initial computer vision task by training the initial neural network with dropout decay, but then train the neural network on training data for the downstream computer vision task without dropout. That is, the system can modify the supervised learning technique after the pre-training to no longer use dropout. Dropout refers to, for one or more layers of a neural network, randomly disabling the nodes in the layer with some specified probability during the processing of any given batch of training examples.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations.

Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers for training a neural network comprising a plurality of neural network layers to perform a downstream computer vision task, each of the plurality of neural network layers having a respective plurality of layer parameters, and the neural network being configured to receive a network input comprising one or more images to and to process the network input to generate a network output for the downstream computer vision task, the method comprising:
pre-training an initial neural network comprising a first subset of the plurality of neural network layers on first training data for an initial computer vision task through supervised learning to determine first values of the respective layer parameters of the first subset of neural network layers, wherein the first subset of the plurality of neural network layers comprises:
a first convolutional neural network layer with weight standardization (WS) followed by a group normalization (GN) layer, wherein the initial neural network comprises the first subset of neural network layers and one or more first additional neural network layers that (i) receive an output generated by the first subset of neural network layers by processing the network input and (ii) process the output generated by the first subset of neural network layers to generate an output for the initial computer vision task, and wherein the GN layer performs group normalization comprising:
receiving as input a feature map comprising a plurality of channels, each comprising a plurality of values;
dividing the plurality of channels into a plurality of groups, wherein for each group, the GN layer (i) computes a mean and a standard deviation of the respective values of the channels within the group and (ii) normalizes each value of the respective channels within the group using the mean and the standard deviation computed for the group; and
generating an output feature map by applying a learned per-channel linear transformation to the normalized values; and
after pre-training the initial neural network comprising the first subset of the plurality of neural network layers on the first training data for the initial computer vision task, training the neural network on second training data for the downstream computer vision task through supervised learning to determine trained values of the respective layer parameters of the first subset of neural network layers from the first values of the respective layer parameters of the first subset of neural network layers, wherein the neural network comprises:
the first subset of neural network layers of the initial neural network comprising the first convolutional neural network layer with WS followed by the GN layer; and
one or more second additional neural network layers that (i) receive the output generated by the first subset of neural network layers by processing the network input and (ii) process the output generated by the first subset of neural network layers to generate the network output for the downstream computer vision task, and
wherein the second training data for the downstream computer vision task contains fewer training examples than the first training data for the initial computer vision task.

2. The method of claim 1, wherein the downstream computer vision task is a medical imaging task and the one or more images in the network inputs for the downstream computer vision task are medical images from a medical domain and the initial computer vision task operates on images from a different domain than the medical domain.

3. The method of claim 2, wherein the initial neural network task is natural object image classification task.

4. The method of claim 2, wherein the medical images are X-ray images.

5. The method of claim 4, wherein the medical imaging task is a chest X-ray interpretation task or a mammography task.

6. The method of claim 2, wherein the medical images are camera images of a portion of a human body.

7. The method of claim 6, wherein the medical imaging task is a skin condition diagnosis task.

8. The method of claim 1, further comprising determining how many training steps to perform during the training of the neural network on the training data for the downstream computer vision task based on a size of the training data for the downstream computer vision task.

9. The method of claim 1, further comprising determining whether to perform a particular data augmentation technique during the training of the neural network on the training data for the downstream computer vision task based on a size of the training data for the downstream computer vision task.

10. The method of claim 1, wherein training the neural network on training data for the downstream computer vision task through supervised learning comprises training the neural network without weight decay.

11. The method of claim 10, wherein pre-training the initial neural network on training data for the initial computer vision task comprises training the initial neural network with weight decay.

12. The method of claim 1, wherein training the neural network on training data for the downstream computer vision task comprises training the neural network without drop out.

13. The method of claim 1, further comprising determining how to resize input images to a fixed resolution during the training of the neural network on the training data for the downstream computer vision task based on an original size of the images in the training data for the downstream computer vision task.

14. The method of claim 13, further comprising:
after the training of the neural network on the training data for the downstream computer vision task, fine-tuning the neural network to operate on images that have a scaled up resolution relative to the fixed resolution.

15. One or more non-transitory computer-readable storage media storing instructions that when executed by one or more computers cause the one or more computers to perform operations for training a neural network comprising a plurality of neural network layers to perform a downstream computer vision task, each of the plurality of neural network layers having a respective plurality of layer parameters, and the neural network being configured to receive a network input comprising one or more images to and to process the network input to generate a network output for the downstream computer vision task, the method comprising:
- pre-training an initial neural network comprising a first subset of the plurality of neural network layers on first training data for an initial computer vision task through supervised learning to determine first values of the respective layer parameters of the first subset of neural network layers, wherein the first subset of the plurality of neural network layers comprises:
  - a first convolutional neural network layer with weight standardization (WS) followed by a group normalization (GN) layer, wherein the initial neural network comprises the first subset of neural network layers and one or more first additional neural network layers that (i) receive an output generated by the first subset of neural network layers by processing the network input and (ii) process the output generated by the first subset of neural network layers to generate an output for the initial computer vision task, and wherein the GN layer performs group normalization comprising:
    - receiving as input a feature map comprising a plurality of channels, each comprising a plurality of values;
    - dividing the plurality of channels into a plurality of groups, wherein for each group, the GN layer (i) computes a mean and a standard deviation of the respective values of the channels within the group and (ii) normalizes each value of the respective channels within the group using the mean and the standard deviation computed for the group; and
    - generating an output feature map by applying a learned per-channel linear transformation to the normalized values; and
- after pre-training the initial neural network comprising the first subset of the plurality of neural network layers on the first training data for the initial computer vision task, training the neural network on second training data for the downstream computer vision task through supervised learning to determine trained values of the respective layer parameters of the first subset of neural network layers from the first values of the respective layer parameters of the first subset of neural network layers, wherein the neural network comprises:
  - the first subset of neural network layers of the initial neural network comprising the first convolutional neural network layer with WS followed by the GN layer; and
  - one or more second additional neural network layers that (i) receive the output generated by the first subset of neural network layers by processing the network input and (ii) process the output generated by the first subset of neural network layers to generate the network output for the downstream computer vision task, and
- wherein the second training data for the downstream computer vision task contains fewer training examples than the first training data for the initial computer vision task.

16. A system comprising one or more computers and one or more storage devices storing instructions that when executed by the one or more computers cause the one or more computers to perform operations for training a neural network comprising a plurality of neural network layers to perform a downstream computer vision task, each of the plurality of neural network layers having a respective plurality of layer parameters, and the neural network being configured to receive a network input comprising one or more images to and to process the network input to generate a network output for the downstream computer vision task, the method comprising:
- pre-training an initial neural network comprising a first subset of the plurality of neural network layers on first training data for an initial computer vision task through supervised learning to determine first values of the respective layer parameters of the first subset of neural network layers, wherein the first subset of the plurality of neural network layers comprises:
  - a first convolutional neural network layer with weight standardization (WS) followed by a group normalization (GN) layer, wherein the initial neural network comprises the first subset of neural network layers and one or more first additional neural network layers that (i) receive an output generated by the first subset of neural network layers by processing the network input and (ii) process the output generated by the first subset of neural network layers to generate an output for the initial computer vision task, and wherein the GN layer performs group normalization comprising:
    - receiving as input a feature map comprising a plurality of channels, each comprising a plurality of values;
    - dividing the plurality of channels into a plurality of groups, wherein for each group, the GN layer (i) computes a mean and a standard deviation of the respective values of the channels within the group and (ii) normalizes each value of the respective channels within the group using the mean and the standard deviation computed for the group; and
    - generating an output feature map by applying a learned per-channel linear transformation to the normalized values; and
- after pre-training the initial neural network comprising the first subset of the plurality of neural network layers on the first training data for the initial computer vision task, training the neural network on second training data for the downstream computer vision task through supervised learning to determine trained values of the respective layer parameters of the first subset of neural network layers from the first values of the respective layer parameters of the first subset of neural network layers, wherein the neural network comprises:
  - the first subset of neural network layers of the initial neural network comprising the first convolutional neural network layer with WS followed by the GN layer; and
  - one or more second additional neural network layers that (i) receive the output generated by the first subset of neural network layers by processing the network input and (ii) process the output generated by the first subset of neural network layers to generate the network output for the downstream computer vision task, and
- wherein the second training data for the downstream computer vision task contains fewer training examples than the first training data for the initial computer vision task.

17. The system of claim 16, wherein the downstream computer vision task is a medical imaging task and the one or more images in the network inputs for the downstream computer vision task are medical images from a medical domain and the initial computer vision task operates on images from a different domain than the medical domain.

18. The system of claim 17, wherein the initial neural network task is natural object image classification task.

19. The system of claim 16, wherein the method further comprises determining how many training steps to perform during the training of the neural network on the training data for the downstream computer vision task based on a size of the training data for the downstream computer vision task.

20. The system of claim 16, wherein the method further comprises determining whether to perform a particular data augmentation technique during the training of the neural network on the training data for the downstream computer vision task based on a size of the training data for the downstream computer vision task.

* * * * *